United States Patent [19]
Nardi et al.

[11] Patent Number: 5,885,956
[45] Date of Patent: Mar. 23, 1999

[54] TREATMENT FOR DIABETES USING A GASTRIN/CCK RECEPTOR LIGAND AND AN EGF RECEPTOR LIGAND

[75] Inventors: Ronald V. Nardi, Sudbury; Stephen J. Brand, Lincoln, both of Mass.

[73] Assignees: Research Triangle Pharmaceuticals; The General Hospital Corporation

[21] Appl. No.: 992,255

[22] Filed: Dec. 14, 1992

[51] Int. Cl.$^6$ .................. A61K 38/16; C07K 14/495

[52] U.S. Cl. .............................. 514/2; 514/866; 530/309; 530/399

[58] Field of Search ................... 514/2, 866, 44; 530/399, 309; 800/2, DIG. 1; 935/13; 424/199.1, 93.21; 435/325, 360, 365.1

[56] References Cited

PUBLICATIONS

L.G. Durrant et al. Brit. J. Cancer 63:67–70 1991.
G.S. Baldwin & Q–X Zhang Cancer Res. 52:2261–74/15/92.
M. Korc J. Clin Invest. 92:1113–4 Sep. 1993.
T.C. Wang et al. J. Clin. Invest. 92:1349–56 Sep. 1993.

*Primary Examiner*—Lorraine Spector
*Attorney, Agent, or Firm*—Rae-Venter Law Group, P.C.

[57] ABSTRACT

A method for treating diabetes mellitus by administering composition providing a gastrin/CCK receptor ligand, e.g. a gastrin, and an EGF receptor ligand, e.g. TGFα, in an amount sufficient to effect differentiation of pancreatic islet precursor cells to mature insulin-secreting cells. The composition can be administered systemically or expressed in situ by cells transgenically supplemented with one or both of a gastrin/CCK receptor ligand gene, e.g. a preprogastrin peptide precursor gene and an EGF receptor ligand gene, e.g. a TGFα gene.

9 Claims, 5 Drawing Sheets

TREATMENT FOR DIABETES USING A GASTRIN/CCK RECEPTOR LIGAND AND AN EGF RECEPTOR LIGAND

BACKGROUND OF THE INVENTION

This invention relates to treatment of diabetes mellitus by effecting the differentiation of pancreatic islet precursor cells into mature insulin-producing cells by the combined synergistic stimulation by a gastrin/cholecystokinin (CCK) receptor ligand, particularly gastrin, and an epidermal growth factor (EGF) receptor ligand, particularly transforming growth factor alpha (TGFα).

The pancreatic islets develop from endodermal stem cells that lie in the fetal ductular pancreatic endothelium, which also contains pluripotent stem cells that develop into the exocrine pancreas. Teitelman, G. and J. K. Lee, *Developmental Biology*, 121: 454–466 (1987); Pictet, R. and W. J. Rutter, *Development of the embryonic endocrine pancreas, in Endocrinology, Handbook of Physiology*, ed. R. O. Greep and E. B. Astwood (1972), American Physiological Society: Washington D.C., p. 25–66. Islet development proceeds through discrete developmental states during fetal gestation which are punctuated by dramatic transitions. The initial period is a protodifferentiated state which is characterized by the commitment of these pluripotent stem cells to the islet cell lineage, as manifested by the expression of insulin and glucagon. These protodifferentiated cells comprise a population of committed islet precursor cells which express only low levels of islet specific gene products and lack the cytodifferentiation of mature islet cells. Pictet, R. and W. J. Rutter, supra. Around day 16 in mouse gestation, the protodifferentiated pancreas begins a phase of rapid growth and differentiation characterized by cytodifferentiation of islet cells and a several hundred fold increase in islet specific gene expression. Histologically, islet formation (neogenesis) becomes apparent as proliferating islets bud from the pancreatic ducts (nesidioblastosis). Just before birth the rate of islet growth slows, and islet neogenesis and nesidioblastosis becomes much less apparent. Concomitant with this, the islets attain a fully differentiated state with maximal levels of insulin gene expression. Therefore, similar to many organs, the completion of cellular differentiation is associated with reduced regenerative potential.

Since differentiation of protodifferentiated precursors occurs during late fetal development of the pancreas, the factors regulating islet differentiation are likely to be expressed in the pancreas during this period. One of the genes expressed during islet development encodes the gastrointestinal peptide, gastrin. Although gastrin acts in the adult as a gastric hormone regulating acid secretion, the major site of gastrin expression in the fetus is the pancreatic islets. Brand, S. J. and P. J. Fuller, *J. Biol Chem.*, 263:5341–5347 (1988). Expression of gastrin in the pancreatic islets is transient. It is confined to the period when protodifferentiated islet precursors form differentiated islets. Although the significance of pancreatic gastrin in islet development is unknown, some clinical observations suggest a role for gastrin in this islet development as follows. For example, hypergastrinemia caused by gastrin-expressing islet cell tumors and atrophic gastritis is associated with nesidioblastosis similar to that seen in differentiating fetal islets. Sacchi, T. B., et al., *Virchows Archiv B*, 48:261–276 (1985); and Heitz, P. U., et al., *Diabetes*, 26:632–642 (1977). Further, an abnormal persistence of pancreatic gastrin has been documented in a case of infantile nesidioblastosis. Hollande E., et al., *Gastroenterology*, 71:255–262 (1976). However, in neither observation was a causal relationship established between the nesidioblastosis and gastrin stimulation.

Citation of a reference herein shall not be construed as an admission that such reference is prior art to the present invention.

SUMMARY OF THE INVENTION

The invention provides a method for treating diabetes mellitus by administering a composition providing a gastrin/CCK receptor ligand, e.g. gastrin, and an EGF receptor ligand, e.g. TGFα, in an amount sufficient to effect differentiation of pancreatic islet precursor cells to mature insulin-secreting cells. The composition can be administered systemically or expressed in situ by cells supplemented with a nucleic acid fusion construct in an expression vector. The fusion construct includes a preprogastrin peptide precursor coding sequence and can also include a coding sequence for an EGF receptor ligand.

In summary, the studies reported below demonstrate that complete islet cell neogenesis has now been reactivated in vivo in mammals in the ductular epithelium of the adult pancreas by stimulation with a gastrin/CCK receptor ligand, such as gastrin, and an EGF receptor ligand, such as TGFα. These studies demonstrate and confirm that both types of growth factors are required to achieve the envisioned objective, neither one alone is sufficient. Studies are reported on the transgenic over-expression of TGFα and gastrin in the pancreas which elucidate the role of pancreatic gastrin expression in islet development and indicate that TGFα and gastrin each play a role in regulating islet development.

Thus, regenerative differentiation of residual pluripotent pancreatic ductal cells into mature insulin-secreting cells has now become a viable clinical option for the treatment of diabetes mellitus, particularly juvenile onset diabetes, by therapeutic administration of this combination of factors or compositions which provide for their in situ expression within the pancreas.

DETAILED DESCRIPTION OF PREFERRED EMBODIMENTS

Figure 1A:
FIG. 1A is an image that shows numerous insulin staining cells in the metaplastic ducts from the TGFα transgenic pancreas upon immunoperoxidase staining.

The present invention is based in part on studies which demonstrate numerous insulin staining cells in the TGFα-induced metaplastic ductules. The low level of exocrine and endocrine gene expression in the metaplastic ductal cells resembles that of protodifferentiated ductal cells seen in the early stage of fetal pancreatic development. Formation of islets (neogenesis) results from proliferation and differentiation of these protodifferentiated insulin expressing cells. Histologically this is manifest as islets appearing to bud from the pancreatic ducts (nesidioblastosis). In the MT-42 TGFα transgenic mice, the ductular metaplasia is not seen in the immediate post-natal period, but only at 4 weeks of age. This indicates that TGFα over-expression induces the insulin expression in duct epithelia rather than prolonging the persistence of islet precursors found in fetal pancreatic ducts.

Although the metaplastic ductules contain numerous insulin positive cells, the islet mass of the TGFα transgenic mice was not increased over controls. Thus, TGFα overexpression alone cannot effect transition of these protodifferentiated duct cells into fully differentiated islets. This implies that islet differentiation requires other factors absent from the adult pancreas of TGFα transgenic mice. Since differentiation of protodifferentiated islet precursors occurs during late fetal development, factors regulating this transition would likely be expressed in islets during this period. Among the factors expressed in the developing islets are the gastrointestinal peptides, the gastrins. Clinical observations have also linked gastrin expression with nesidioblastosis—budding of proliferating islets from fetal pancreatic ducts. See Hollande, et al, *Gastroenterology,* 71:255–262 (1976) and Sacchi, T. B., et al., *Virchows Archiv B,* 48:261–276 (1985).

As used herein, the term "gastrin/CCK receptor ligand" encompasses compounds that stimulate the gastrin/CCK receptor such that when EGF receptors in the same or adjacent tissue or in the same individual are also stimulated, neogenesis of insulin-producing pancreatic islet cells is induced. Examples of such gastrin/CCK receptor ligands include various forms of gastrin such as gastrin 34 (big gastrin), gastrin 17 (little gastrin), and gastrin 8 (mini gastrin); various forms of cholecystokinin such as CCK 58, CCK 33, CCK 22, CCK 12 and CCK 8; and other gastrin/CCK receptor ligands that demonstrate the same synergistic activity with EGF receptor ligands and have a carboxy terminal peptide Trp-Met-Asp-Phe-amide which can induce differentiation of cells in mature pancreas to form insulin-secreting islet cells, when acting synergistically with an EGF receptor ligand. Also contemplated are active analogs, fragments and other modifications of the above. Such ligands also include compounds that increase the secretion of endogenous gastrins, cholecystokinins or similarly active peptides from sites of tissue storage. Examples of these are omeprazole which inhibits gastric acid secretion and soya bean trypsin inhibitor which increases CCK stimulation.

As used herein, the term "EGF receptor ligand" encompasses compounds that stimulate the EGF receptor such that when gastrin/CCK receptors in the same or adjacent tissue or in the same individual are also stimulated, neogenesis of insulin-producing pancreatic islet cells is induced. Examples of such EGF receptor ligands include EGF1-53 including EGF1-48, EGF1-52, EGF1-49 and fragments and active analogs thereof. Other examples include TGFα receptor ligands (1-50) that includes 1-48, 1-47 and other EGF receptor ligands such as amphiregulin and pox virus growth factor as well as other EGF receptor ligands that demonstrate the same synergistic activity with gastrin/CCK receptor ligands. These include active analogs, fragments and modifications of the above. For further background, see Carpenter and Wahl, Chapter 4 in Peptide Growth Factors (Eds. Sporn and Roberts), Springer Verlag, 1990.

A principal aspect of the invention is a method for treating diabetes mellitus in an individual in need thereof by administering to the individual a composition including a gastrin/CCK receptor ligand and an EGF receptor ligand in an amount sufficient to effect differentiation of pancreatic islet precursor cells to mature insulin-secreting cells. The cells differentiated are residual latent islet precursor cells in the pancreatic duct. The method is principally for treating juvenile-onset diabetes mellitus. One embodiment comprises administering, preferably systemically, a differentiation regenerative amount of gastrin and an EGF receptor ligand, preferably TGFα, to the individual.

Another embodiment comprises administering a gastrin/CCK receptor ligand and EGF receptor ligand to pancreatic islet precursor cells of explanted pancreatic tissue of the mammal and reintroducing the pancreatic tissue so stimulated to the mammal. Again here, the gastrin/CCK receptor ligand is preferably gastrin and the EGF receptor ligand is preferably TFGα.

In another embodiment gastrin/CCK receptor ligand stimulation is effected by expression of a chimeric insulin promoter-gastrin fusion gene construct transgenically introduced into such precursor cells. In another embodiment EGF receptor ligand stimulation is effected by expression of a EGF receptor ligand gene transgenically introduced into the mammal. Preferably, the EGF receptor ligand is TGFα and the EGF receptor ligand gene is a TGFα gene.

In another embodiment stimulation by gastrin/CCK receptor ligand and EGF receptor ligand is effected by coexpression of (i) a preprogastrin peptide precursor gene and (ii) an EGF receptor ligand gene that have been stably introduced into the mammal. Here again, the EGF receptor ligand is preferably TGFα and the EGF receptor ligand gene is preferably a TGFα gene.

In another aspect the invention relates to a method for effecting the differentiation of pancreatic islet precursor cells of a mammal by stimulating such cells with a combination of a gastrin/CCK receptor ligand, particularly gastrin, and an EGF receptor ligand, particulary TGFα. In a preferred embodiment of this aspect, gastrin stimulation is effected by expression of a preprogastrin peptide precursor gene stably introduced into the mammal. The expression is under the control of the insulin promoter. EGF receptor ligand, e.g. TGFα, stimulation is effected by expression of an EGF receptor ligand gene transgenically introduced into the mammal. In furtherance of the above, stimulation by gastrin and TGFα is preferably effected by co-expression of (i) a preprogastrin peptide precursor gene and (ii) a EGF receptor ligand, e.g. TGFα, gene that have been stably introduced into the mammal.

Another aspect of the invention is a nucleic acid fusion construct. This construct includes a nucleic acid sequence coding for the preprogastrin peptide precursor and an insulin transcriptional regulatory sequence, which is 5' to and effective to support transcription of a sequence encoding the preprogastrin peptide precursor. Preferably, the insulin transcriptional regulatory sequence includes at least the insulin promoter. In a preferred embodiment the nucleic acid sequence coding for the preprogastrin peptide precursor comprises a polynucleotide sequence containing exons 2 and 3 of the human gastrin gene and optionally also including introns 1 and 2.

Another embodiment of the invention is a composition comprising (i) a nucleic acid sequence coding for a mammalian EGF receptor ligand, e.g., TGFα and a transcriptional regulatory sequence therefor; and (ii) a nucleic acid sequence coding for the preprogastrin peptide precursor and a transcriptional regulatory sequence therefor. Preferably, the transcriptional regulatory sequence for the EGF receptor ligand is a strong non-tissue specific promoter, such as the metallothionene promoter. Preferably, the transcriptional regulatory sequence for the preprogastrin peptide precursor is the insulin promoter. A preferred form of this embodiment is one wherein the nucleic acid sequence coding for the preprogastrin peptide precursor comprises a polynucleotide sequence containing introns 1 and 2 and exons 2 and 3 of the human gastrin gene.

Another aspect of the invention relates to a vector including the fusion gene construct comprising the preprogastrin peptide precursor coding sequence. This vector can be a plasmid such as the pGem1 or can be a phage which has a transcriptional regulatory sequence including the insulin promoter.

Another aspect of this invention relates to a composition of vectors including one having the nucleic acid sequence coding for a mammalian EGF receptor ligand, e.g., TGFα, under control of a strong non-tissue specific promoter, e.g., the metallothionene promoter; and (ii) a preprogastrin peptide precursor coding sequence under control of the insulin promoter. Each vector can be a plasmid, such as plasmid pGem1 or a phage in this aspect.

Another aspect of the invention is a non-human mammal or tissue, including cells, thereof capable of expressing a stably integrated gene which encodes preprogastrin. Another embodiment of this aspect is a non-human mammal capable of coexpressing (i) a preprogastrin peptide precursor gene; and (ii) an EGF receptor ligand, e.g. TGFα, gene that have been stably integrated into the mammal, mammalian tissue or cells.

Therapeutic Administration and Compositions

Modes of administration include but are not limited to transdermal, intramuscular, intraperitoneal, intravenous, subcutaneous, intranasal, and oral routes. The compounds may be administered by any convenient route, for example by infusion or bolus injection by absorption through epithelial or mucocutaneous linings (e.g., oral mucosa, rectal and intestinal mucosa, etc.) and may be administered together with other biologically active agents. Administration is preferably systemic.

The present invention also provides pharmaceutical compositions. Such compositions comprise a therapeutically effective amount of a therapeutic, and a pharmaceutically acceptable carrier or excipient. Such a carrier includes but is not limited to saline, buffered saline, dextrose, water, glycerol, ethanol, and combinations thereof. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

Various delivery systems are known and can be used to administer a therapeutic of the invention, e.g., encapsulation in liposomes, microparticles, microcapsules and the like.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ameliorate any pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the therapeutic of the invention which will be effective in the treatment of a particular disorder or condition will depend on the nature of the disorder or condition, and can be determined by standard clinical techniques. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

Materials and Methods

The following materials and methods were used in the studies reported by the working examples set forth below except as otherwise noted.

Animals

Mice, FVB and CD strain, were obtained from Taconic Farms, Inc., Germantown, NY. The TGFα transgenic line MT-42 used, which expresses high levels of TGFα from a metallothionine promoter, is described in Jhappan et al, *Cell*, 61:1137–1146 (1990).

INSGAS Transgene Construct

A Pvull-Rsal fragment encompassing nucleotides −370 to +38 of the rat insulin I gene (Cordell, B. G. et al, *Cell*, 18:533–543, 1979) was ligated into pGem1 (Promega Corp., Madison, Wis.). A 4.4 kb Bam Hl-EcoRl fragment containing 1.5 kb introns 1 and 2 and exons 2 and 3 of the human gastrin gene which encodes the preprogastin peptide precursor was isolated and subcloned downstream of the rat insulin I fragment in pGem1 (Promega). The fragment is described in Wiborg, O., Proc. Natl. Acad. Sci. USA, 81:1067–1069 (1984) and Ito, R., et al, Proc. Natl. Acad. Sci. (USA), 81:4662–4666 (1984). The insulin promoter-preprogastrin INSGAS transgene construct was excised as a 4.8 kb Xbal-EcoRl fragment.

Generation and Characterization of Transgenic Mice

The fragment, made as described above was prepared for microinjection as follows. It was isolated by agarose gel electrophoresis, purified by CsCl gradient purification, and dialyzed extensively against injection buffer (5 mM NaC1; 0.1 mM EDTA; 5 mM Tris-HCl pH 7.4). Fertilized oocytes from FVB inbred mice (Taconic Farms, Inc., supra) at the single-cell stage were microinjected using standard techniques. See Hogan, B., et al., *Manipulating the mouse embryo: A laboratory manual,* Cold Spring Harbor, N.Y. (1986). Surviving embryos were then implanted into the oviducts of CD1 (Charles River Laboratories, Inc., Wilmington, Mass.) foster mothers according to procedures in Hogan, et al. Transgenic founder mice were identified by DNA blot techniques using DNA isolated from individual mouse tails, and a human gastrin exon 2 probe labelled with 32 dCTP by random priming. F1 mice and their siblings were similarly identified.

Homozygous MT-42 mice containing the MT-TGFα transgene derived from a CD-1 mouse strain (Jhappan, supra) were crossed with heterozygotic INSGAS mice. After weaning, the offspring were placed on acidified 50 mM $ZnCl_2$ as previously described in order to induce the metallothionine promoter (Jhappan, supra).

Northern Blot Hybridization Assay.

For Northern analysis, total RNA was extracted from tissues by the method of Cathala et al, *DNA,* 2:329–335 (1983). Samples of 20 μg of total RNA were resolved on a 1% agarose denaturing gel and transferred to nitrocellulose. RNA blots were hybridized with $^{32}P$ labelled TGFα riboprobes or exon 2 of human gastrin that did not cross-hybridize with endogenous mouse gastrin mRNA.

Peptide Radioimmunoassay of Gastrin

Tissues were extracted and assayed for gastrin immunoreactivity by radioimmunoassay as described previously using antibody 2604 which is specific for biologically active C terminally amidated gastrin in a gastrin radioimmunoassay as described in Rehfeld, J. F., Scand. J. Clin. Lab. Invest, 30:361–368 (1972). Tyrosine monoiodinated human gastrin 17 tracer was used in all assays and synthetic human gastrin 17 was used as a standard.

Peptide Radioimmunoassay of TGFα

Tissues were frozen in liquid nitrogen, ground to powder with mortar and pestle, and subjected to acid-ethanol extraction as described in Todaro, G. J., et al Proc. Natl. Acad. Sci. USA, 77:5258–5262 (1980). Extracts were reconstituted with water, and protein concentrations determined with a Coomassie blue dye binding assay (Bio-Rad Laboratories, Hercules, Calif.). Aliquots from the pancreata were tested in duplicate in a TGFα radioimmunoassay, which measured competition with $^{125}I$ TGFα for binding to a solid-phase rabbit antibody raised against the C-terminus of rat TGFα (kit from BioTope, Seattle, Wash.).

Histological Analysis

The pancreas was removed, weighed, similarly oriented in cassettes, fixed in Bouin's solution and embedded in paraffin by conventional procedures.

Tissue Preparation and Immunohistochemistry

Freshly excised pancreases were dissected, cleared of fat and lymph nodes, fixed in Bouin's fixative, and then embedded in paraffin for sectioning. Routine sections were stained with hematoxylin and eosin according to standard methods. Pancreatic tissue from adult 17 week old MT-TGFα (MT-42) transgenic mice were immunostained for insulin to examine the effect of TGFα over-expression on islet development. Insulin positive cells in TGFα-induced metaplastic ductules using immunoperoxidase staining guinea pig anti-human insulin sera (Linco, Eureka, Mo.; a pre-immune guinea pig serum was used as a control. Immunohistochemistry was performed on 5u paraffin sections by the peroxidase/antiperoxidase method of Sternberger using a monoclonal rabbit antigastrin antibody. See, Sternberger, L. A., Immunocytochemistry, 2nd ed. 1979, NY: Wiley. p 104–170.

Point-Counting Morphometrics

The relative volume of islets, ducts, or interstitial cells was quantitated using the point-counting method described in Weibel, E. R., Lab Investig., 12:131–155 (1963). At a magnification of 400×, starting at a random point at one corner of the section, every other field was scored using a 25 point ocular grid. An unbiased but systematic selection of fields was accomplished using the markings of the stage micrometer. Intercepts over blood vessels, fat, ducts, lymph nodes, or interlobular space were subtracted to give the total pancreatic area. A minimum of 5000 points in 108 fields (systematically chosen using the stage micrometer) were counted in each block, with the relative islet volume being the number of intercepts over islet tissue divided by the number over pancreatic tissue. The absolute islet mass or islets was calculated as the relative islet volume times pancreatic weight. See, Lee, H. C., et al, Endocrinology, 124:1571–1575 (1989).

Statistical Analysis

Differences between means were compared for significant differences using the Student's t test for unpaired data.

EXAMPLE 1

Assay For Insulin Production in TGF Transgenic Pancreas

Figure 1B:
FIG. 1B is an image that shows that most ductular cells stained less intensely for insulin, while occasional ductular cells did stain with the same intensity of insulin staining as the adjacent islets.

Immunoperoxidase staining showed numerous insulin staining cells in the metaplastic ducts from the TGFα transgenic pancreas (FIG. 1A), whereas insulin staining cells were virtually absent from the non-transgenic ducts (less than 6.1%). When at least 600 ductular cells/animal were scored at final magnification of 400×, insulin positive cells were seen at a frequency of 6.0±0.9% (n=5) in the metaplastic ductules of TGFα transgenic mice. Occasional ductular cells stained with the same intensity of insulin staining as the adjacent islets, but most had less intense staining (Figure 1B). The low level of insulin staining of the ductular cells resembles that of protodifferentiated cells reported in the ducts of the developing pancreas. Pictet, R. and W. J. Rutter, *Development of the embryonic endocrine pancreas, in Endocrinology, Handbook of Physiology*, ed. R. O. Greep and E. B. Astwood, 1972, American Physiological Society: Washington, D.C. p. 25–66; and Alpert, S., et al. Cell, 53:295–308, 1988.

However, despite the increased number of insulin positive cells in the metaplastic ducts, the islet mass of the TGFα transgenic mice was not increased. The islet mass as quantitated by point counting morphometrics was 2.14 mg ±0.84 (mean±se, n=5) in the TGFα transgenic pancreas compared to 1.93 mg ±0.46 (n=6) non transgenic litter mates.

One interpretation of these findings is that TGFα overexpression causes proliferation of protodifferentiated precursors but cannot alone effect the transition of these protodifferentiated cells into fully differentiated islets, differentiation being regulated by other factors absent from the adult pancreas.

EXAMPLE 2

Pancreatic Gastrin Expression from the INSGAS Transgene

Figure 2A:
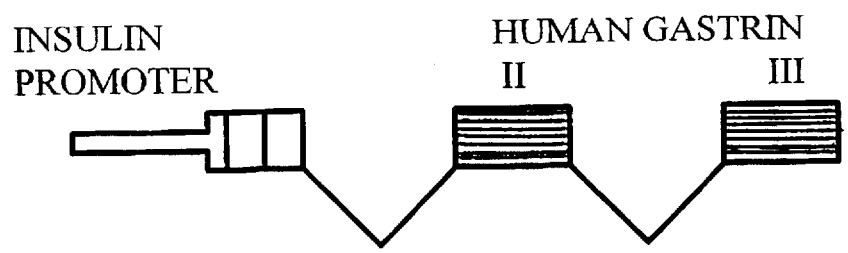
FIG. 2A schematically shows the structure of the chimeric insulin promoter-gastrin (INSGAS) transgene.

To examine the possible role of gastrin in regulating islet differentiation, transgenic mice were created that express a chimeric insulin promoter-gastrin (INSGAS) transgene in which the insulin promoter directs pancreas specific expression of the gastrin transgene (FIG. 2A). Unlike the gastrin gene, insulin gene expression is not switched off after birth. Thus, the INSGAS transgene results in a persistence of gastrin expression in the adult pancreas.

The INSGAS transgene comprised 370 bp of 5' flanking DNA and the first non-coding exon of the rat insulin I gene. Cordell, B., et al., Cell, 18:533–543, 1979. It was ligated to a Bam H1-EcoR1 fragment containing 1.5 kb intron 1 and exons 2 and 3 of the human gastrin gene which encodes the preprogastin peptide precursor. Wiborg, 0., et al., Proc. Natl. Acad. Sci. USA, 81:1067–1069, 1984; and Ito, et al. Proc. Natl. Acad. Sci. USA, 81:4662–4666, 1984. A 4.8 kb INSGAS fragment was isolated and microinjected into inbred FVB, one cell mouse embryos. Hogan, B. et al., *Manipulating the mouse embryo: A laboratory manual*, 1986, NY:Cold Spring Harbor.

Gastrin immunoreactivity in pancreatic and stomach extracts from transgenic and non-transgenic mice was assayed by radioimmunoassay using antisera 2604 (Rehfeld, J., et al., Scand. J. Clin. Lab. Invest., 30: 361–368, 1972) specific for the bioactive amidated C-terminus of gastrin.

Beta cell specific gastrin expression from the INSGAS transgene was observed based on immunostaining of pancreatic tissues with a gastrin monoclonal antibody.

Figure 2B:
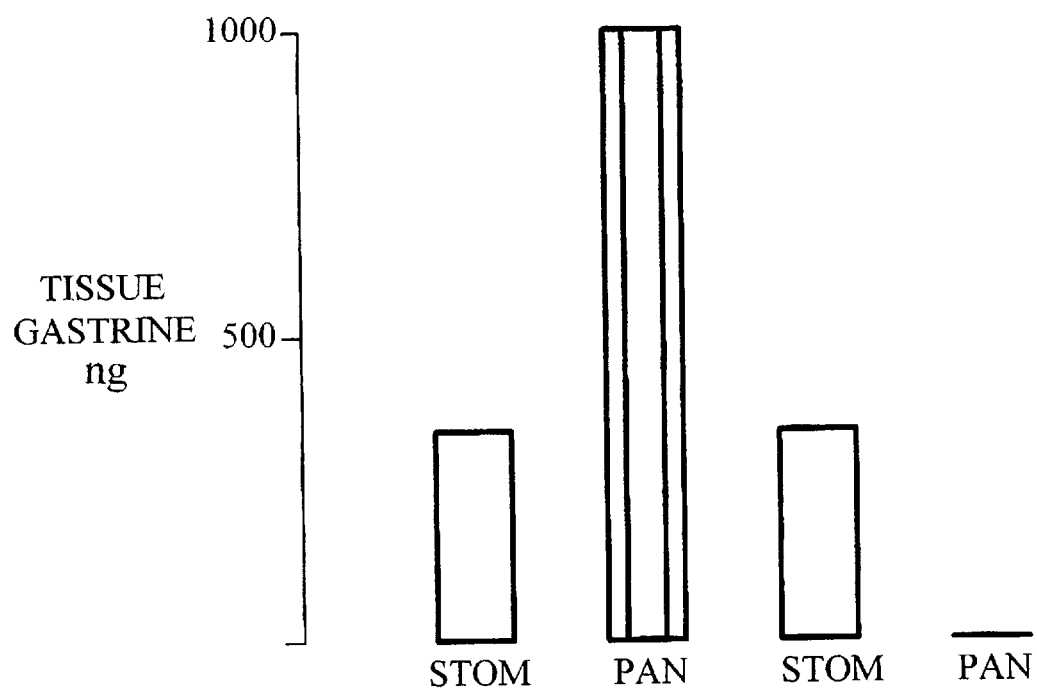
FIG. 2B illustrates that the radioimmunoassay of pancreatic extracts from INSGAS transgenic mice shows high levels of gastrin immunoreactivity that exceed the gastrin content in the gastric antrum expressed from the endogenous murine gene. The INSGAS transgenic mice had high expression of gastrin in the postnatal pancreas.

Northern blots of RNA isolated from different tissues of 8 week old INSGAS transgenic mice were hybridized with a human gastrin exon 2 probe. High levels of gastrin transgene mRNA were seen in the pancreas but not in any other tissues. This probe is specific for the human gastrin gene; no hybridization is seen in antral RNA of INSGAS and non-transgenic FVB mice express high levels of murine gastrin mRNA. Radioimmunoassay of pancreatic extracts from INSGAS transgenic mice shows high levels of gastrin immunoreactivity that exceed the gastrin content in the gastric atrium expressed from the endogenous murine gene (FIG. 2B). No gastrin immunoreactivity was detected in pancreatic extracts of non-transgenic control mice FIG. 2B. The gastrin radioimmunoassay is specific for carboxy amidated precursors, indicating that the gastrin peptide precursor is efficiently processed post-translationally to the bioactive peptide. Immunohistochemistry with a gastrin monoclonal antibody shows pancreatic beta islet cell specific expression of gastrin.

Although the INSGAS transgenic mice had high expression of gastrin in the postnatal pancreas (FIG. 2B), the INSGAS transgenic mice had pancreatic histology identical to controls. Islet mass as quantitated by point-counting morphometrics (Weibel, E. R., Lab Investig., 12:131–155, 1963) was identical in 5–6 week old INSGAS mice (1.78±0.21 mg, n=1 1) and age matched non-transgenic controls (1.74±19 mg, n=1 1). Thus, sustained expression of gastrin in the postnatal pancreas alone does not stimulate islet cell growth.

EXAMPLE 3

Histological Examination of TGFα and TGFα/INSGAS Pancreas

Stimulation of islet growth by gastrin may require stimulation by other growth factors to create a responsive population of cells. Therefore, effects of gastrin stimulation were studied in TGFα transgenic mice which have metaplastic ducts that contain insulin expressing cells resembling protodifferentiated islet-precursors. To assess the interaction between gastrin and TGFα, three groups of mice were bred with equivalent FVB/CD1 strain genetic backgrounds: non-transgenic control, TGFα single transgenic and INSGAS/TGFα double transgenics. All three groups of mice were placed on 50 mM $ZnCl_2$ at 3 weeks of age. At 17 weeks of age, the animals were sacrificed and the pancreas removed for histological evaluation. The pancreas from TGFα and INSGAS/TGFα mice had similar gross morphological appearances: resilient, firm and compact in contrast to the soft diffuse control pancreas. TGFα expression was equivalent in TGFα and INSGAS/TGFα groups when measured by Northern blot analysis (data not shown) and by radioimmunoassay. The pancreatic TGFα immunoreactive peptide levels were 12.2±1 and 18.9±8 nq/mg protein (Mean±SD) in the TGFα and INSGAS/TGFα mice, respectively.

Figure 3A:
FIG. 3A is an image of the pancreatic histology of an INSGAS/TGFα mouse used in the study reported by Example 3. The INSGAS/TGFα pancreas had some areas of increased ductular complexes and slightly increased interstitial cellularity. The field shown here had the most severly abnormal histology in the five animals used.
Figure 3B:
FIG. 3B an image of the pancreatic histology of a control mouse from Example 3.

Light micrographs of hematoxylin stained paraffin sections of pancreas from the three groups of mice studied; (A: INSGAS/TGFα; B: FVB/CD1 controls; and C: TGFα) were made. The INSGAS/TGFα pancreas had some areas of increased ductular complexes and slightly increased interstitial cellularity; the field shown (FIG. 3A) had the most severely abnormal morphology seen in the five animals; most of the pancreas was indistinguishable from controls (FIG. 3B). In contrast, the field of TGFα pancreas (FIG. 3C) was typical and showed the interstitial cellularity and fibrosis combined with florid ductular metaplasia described by Jhappan et al., supra.

Pancreatic gastrin synergistically interacts with TGFα to increase islet mass and inhibit the ductular metaplasia induced by TGFα over-expression. Mating the homozygous MT-TGFα (MT-42) mice (TGFα) with heterozygotic INS- GAS mice gave offspring that were either heterozygotic TGFα single transgenic or double transgenic containing both INSGAS and TGFα transgenes (INSGAS/TGFα). Since INSGAS were FVB strain and TGFα were CD1 strain, TGFα homozygotes and CD1 controls (CON) were both mated with FVB to produce FVB/CD1 strain background for all three groups of mice. Mice were treated with 50 mM $ZnCl_2$ from 3 weeks until sacrifice at age 17 weeks. Pancreas was removed, weighed, similarly oriented in cassettes, fixed in Bouin's solution and embedded in paraffin. One random section from each animal was used to quantitate the relative volumes of ductules and islets by point-counting morphometrics (Weibel, E. R., Lab Investig., 12:131–155, 1963). At least 2000 points over tissue were counted as intercepts of a 50 point grid at 170× magnification; the entire section was covered without overlap. Mass of ductules or islet was calculated by multiplying the relative volume and the animal's pancreatic weight. To normalize different mean body weights, the mass was expressed as ug/g body weight. Results are mean and standard errors for 5–6 animals in each group. * $P<0.05$ (Student's t unpaired data).

Figure 3C:
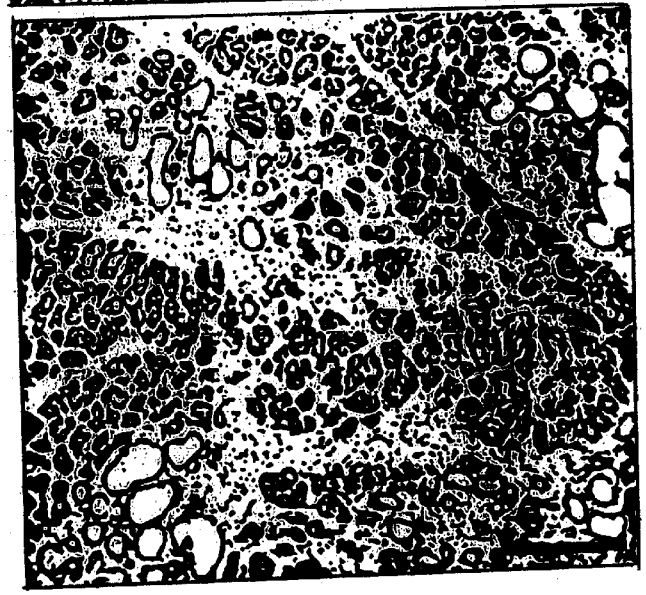
FIG. 3C is an image of the pancreatic histology of a TGFα mouse from Example 3. This field of TGFα pancreas of the study reported in Example 3 was typical and showed the interstitial cellularity and fibrosis combined with florid ductular metaplasia and has been described by Jhappan, et al. supra.

Expression of gastrin from the INSGAS transgene reduced the ductular metaplasia caused by TGFα overexpression. At 17 weeks, the pancreatic histology of the INSGAS/TGFα mice (FIG. 3A) resembled that of the control pancreas (FIG. 3B) more than that of the TGFα mice (FIG. 3C).

Figure 4A:
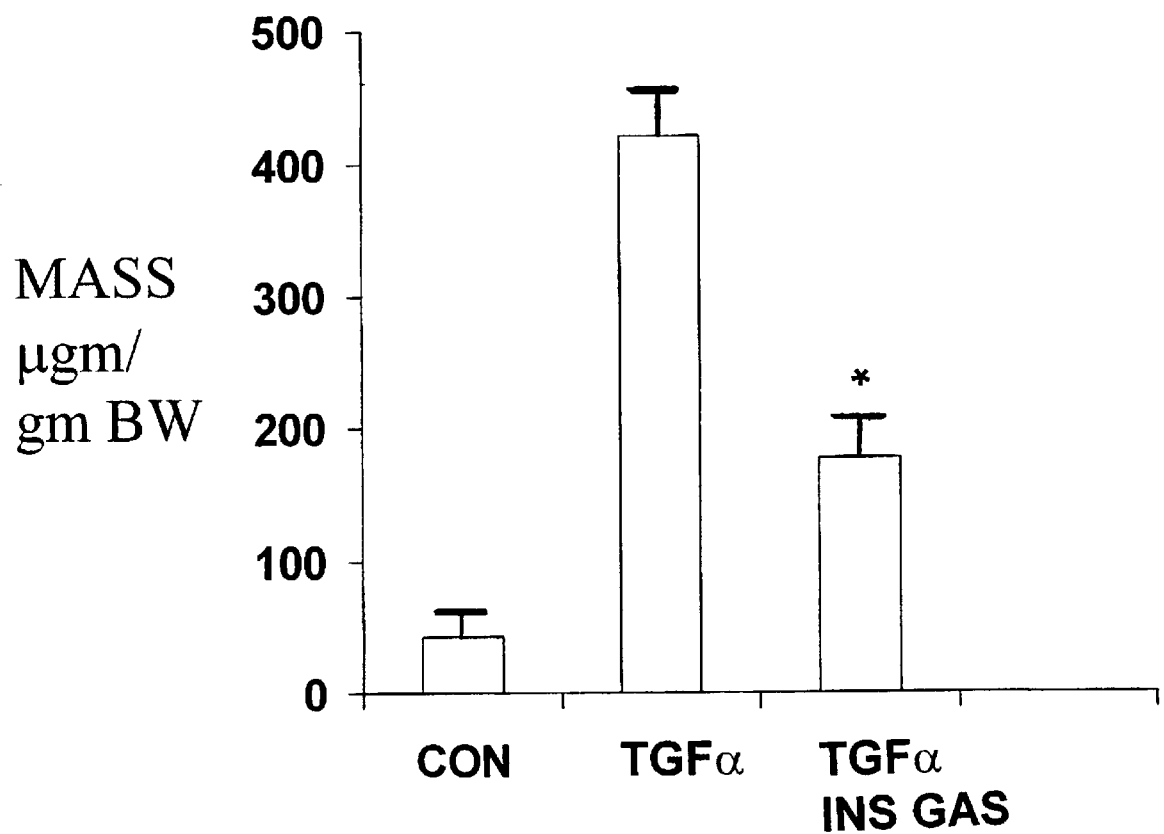
FIG. 4A is a histogram graphically illustrating point=counting morphometric data which confirmed that at 17 weeks the pancreas of the INSGAS/TGFα mice had lower duct mass than the pancreas of the TGFα mice based on the study reported in Example 3.
Figure 4B:
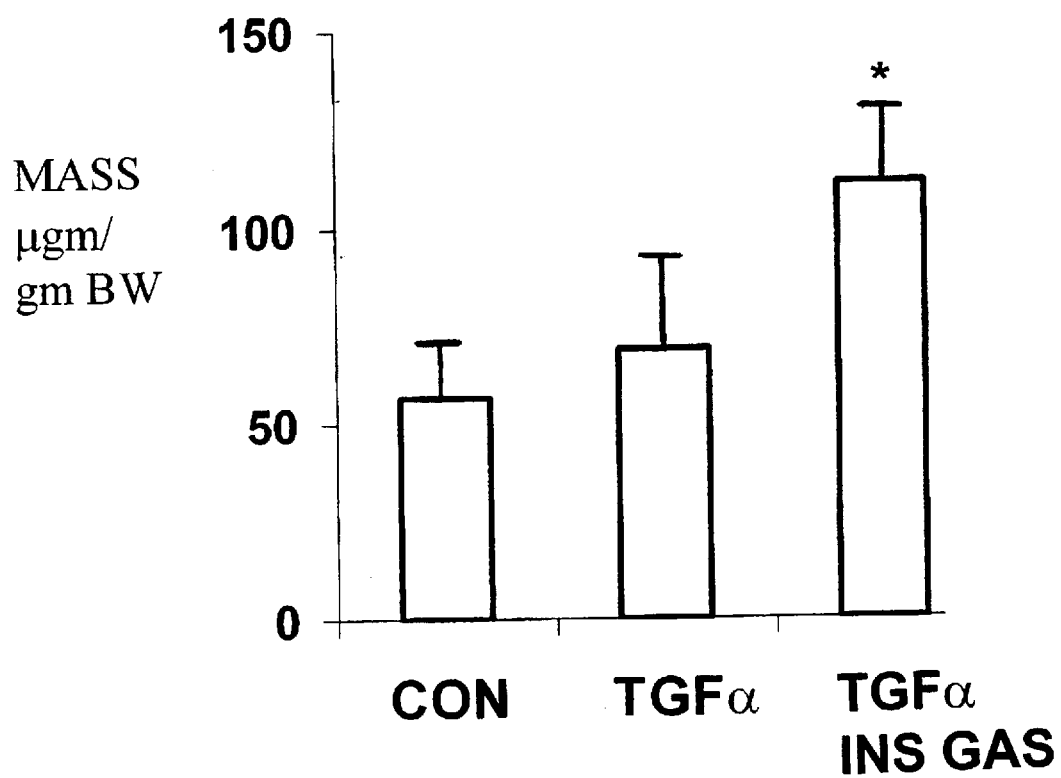
FIG. 4B is a histogram which graphically illustrates point=counting morphometric data which show that co-expression of gastrin and TGFα in the INSGAS/TGFα pancreas significantly increased the islet mass compared to the islet mass of the corresponding non-transgenic control mice. Further, TGFα expression alone does not increase islet mass. These data are based on the studies illustrated in Example 3.

This was confirmed by quantitating pancreatic ductular mass in the TGFα and INSGAS/TGFα transgenic mice and the FVB1/CD1 controls by point-counting morphometrics (FIG. 4A). Co-expression of gastrin and TGFα in the INSGAS/TGFα pancreas also significantly increased the islet mass compared to controls (FIG. 4B), whereas islet mass was not increased by expression of the TGFα or gastrin transgenes alone. The blood glucose concentration was not significantly different between the three groups of mice.

The present invention is not limited by the specific embodiments described herein. Modifications that become apparent from the foregoing description and accompanying figures fall within the scope of the claims.

Various publications are cited herein, the disclosures of which are incorporated by reference in their entireties.

What is claimed is:

1. A method for treating diabetes mellitus in an individual in need thereof which comprises administering to the individual a composition comprising a proteinaceous gastrin/CCK receptor ligand and a proteinaceous EGF receptor ligand in an amount sufficient to effect differentiation of pancreatic islet precursor cells to mature insulin-secreting cells, wherein said composition is administered systemically.

2. The method of claim 1, wherein the cells so differentiated are islet precursor cells in the pancreatic duct.

3. The method of claim 1 which is a method for treating juvenile-onset diabetes mellitus.

4. The method of claim 1 wherein the proteinaceous gastrin/CCK receptor ligand is a gastrin.

5. The method of claim 1 wherein the proteinaceous EGF receptor ligand is TGFα.

6. A method for stimulating pancreatic islet cell neogenesis, the method comprising administering to an individual a composition comprising a proteinaceous gastrin/CCK receptor ligand and a proteinaceous EGF receptor ligand in an amount sufficient to effect differentiation of pancreatic islet precursor cells to mature insulin-secreting islet cells, wherein said composition is administered systemically.

7. The method of claim 6 which is a method for treating diabetes mellitus.

8. The method of claim 6 wherein the proteinaceous gastrin/CCK receptor ligand is gastrin.

9. The method of claim 6 wherein the proteinaceous EGF receptor ligand is TGFα.

* * * * *

UNITED STATES PATENT AND TRADEMARK OFFICE
CERTIFICATE OF CORRECTION

PATENT NO. : 5,885,956
DATED : March 23, 1999
INVENTOR(S): Ronald V. Nardi, Stephen J. Brand
TITLE : TREATMENT FOR DIABETES USING A GASTRIN/CCK RECEPTOR LIGAND AND AN EGF RECEPTOR LIGAND

It is certified that error appears in the above-identified patent and that said Letters Patent is hereby corrected as shown below:

In column 1, line 4, should read

--<u>GOVERNMENT LICENSE RIGHTS</u>

This invention was made with U.S. Government support under Contract 5 R01 DK 42147-04 awarded by the National Institutes of Health. The U.S. Government has certain rights in this invention.--.

Signed and Sealed this

Tenth Day of April, 2001

Attest:

NICHOLAS P. GODICI

*Attesting Officer*   *Acting Director of the United States Patent and Trademark Office*